United States Patent
Hatib et al.

(10) Patent No.: US 7,422,562 B2
(45) Date of Patent: Sep. 9, 2008

(54) REAL-TIME MEASUREMENT OF VENTRICULAR STROKE VOLUME VARIATIONS BY CONTINUOUS ARTERIAL PULSE CONTOUR ANALYSIS

(75) Inventors: Feras Hatib, Irvine, CA (US); Luchy Roteliuk, Lake Forest, CA (US)

(73) Assignee: Edwards Lifesciences, Irvine, CA (US)

( * ) Notice: Subject to any disclaimer, the term of this patent is extended or adjusted under 35 U.S.C. 154(b) by 533 days.

(21) Appl. No.: 11/085,957

(22) Filed: Mar. 22, 2005

(65) Prior Publication Data

US 2005/0187481 A1    Aug. 25, 2005

Related U.S. Application Data

(63) Continuation-in-part of application No. 10/890,887, filed on Jul. 14, 2004, and a continuation-in-part of application No. 10/728,705, filed on Dec. 5, 2003, now Pat. No. 7,220,230.

(51) Int. Cl.
*A61B 5/02* (2006.01)
(52) U.S. Cl. ...................................... 600/485
(58) Field of Classification Search .................. 600/485
See application file for complete search history.

(56) References Cited

U.S. PATENT DOCUMENTS

| | | | |
|---|---|---|---|
| 4,236,527 | A | 12/1980 | Newbower et al. |
| 4,429,701 | A | 2/1984 | Goor et al. |
| 4,507,974 | A | 4/1985 | Yelderman |
| 4,535,774 | A | 8/1985 | Olson |

(Continued)

FOREIGN PATENT DOCUMENTS

EP    393 228 A1    10/1990

(Continued)

OTHER PUBLICATIONS

Antonutto, G.; Girardos, M.; Tuniz, D.; di Prampero, P.E.; "Noninvasive assessment of cardiac output from arterial pressure profiles during exercise"; European Journal of Applied Physiology, 72 (1995), 18-24.

(Continued)

*Primary Examiner*—Robert L. Nasser, Jr.
*Assistant Examiner*—Karen E Toth
(74) *Attorney, Agent, or Firm*—Gregory J. Carlin

(57) ABSTRACT

Ventricular stroke volume variation (SVV) is estimated as a function of the standard deviation of arterial blood pressure value measured over each of at least two cardiac cycles, preferably over each of the cardiac cycles in a computation interval covering a full respiratory cycle. In one embodiment, maximum and minimum standard deviation values are determined over the computation interval. SVV is then estimated proportional to the ratio of the difference between the maximum and minimum standard deviation values and the mean of the standard deviation values. In another embodiment, SVV is then estimated proportional to the ratio of the standard deviation of the standard deviation values and the mean standard deviation over the entire computation interval. A preprocessing arrangement for improving reliability of estimates of more general cardiac or hemodynamic parameters is also disclosed and involves smoothing with an approximating function, and sampling and low-pass filtering at an adjustable rate.

18 Claims, 4 Drawing Sheets

U.S. PATENT DOCUMENTS

| | | | |
|---|---|---|---|
| 4,562,843 A | 1/1986 | Djordjevic et al. | |
| 4,595,015 A | 6/1986 | Jansen et al. | |
| 4,798,211 A | 1/1989 | Goor et al. | |
| 4,834,107 A | 5/1989 | Warner | |
| 5,101,828 A | 4/1992 | Welkowitz et al. | |
| 5,146,414 A | 9/1992 | McKown et al. | |
| 5,178,151 A | 1/1993 | Sackner et al. | |
| 5,183,051 A | 2/1993 | Kraidin et al. | |
| 5,199,438 A | 4/1993 | Pearlman | |
| 5,211,177 A | 5/1993 | Chesney et al. | |
| 5,241,966 A | 9/1993 | Finkelstein et al. | |
| 5,265,011 A | 11/1993 | O'Rourke | |
| 5,265,615 A | 11/1993 | Frank et al. | |
| 5,316,004 A | 5/1994 | Chesney et al. | |
| 5,390,679 A | 2/1995 | Martin | |
| 5,400,793 A | 3/1995 | Wesseling | |
| 5,423,323 A | 6/1995 | Orth | |
| 5,526,817 A | 6/1996 | Pfeiffer et al. | |
| 5,533,511 A | 7/1996 | Kaspari et al. | |
| 5,535,753 A | 7/1996 | Petrucelli et al. | |
| 5,584,298 A | 12/1996 | Kabal et al. | |
| 5,634,467 A | 6/1997 | Nevo | |
| 5,638,823 A | 6/1997 | Akay et al. | |
| 5,647,369 A | 7/1997 | Petrucelli et al. | |
| 5,687,733 A | 11/1997 | McKown | |
| 5,730,138 A | 3/1998 | Wang | |
| 5,743,268 A | 4/1998 | Kabal et al. | |
| 5,746,698 A | 5/1998 | Bos et al. | |
| 5,769,082 A | 6/1998 | Perel | |
| 5,797,395 A | 8/1998 | Martin | |
| 5,830,131 A | 11/1998 | Caro et al. | |
| 5,865,758 A | 2/1999 | Louzianine | |
| 5,876,347 A | 3/1999 | Chesney et al. | |
| 5,913,826 A | 6/1999 | Blank | |
| 6,004,274 A | 12/1999 | Nolan et al. | |
| 6,010,457 A | 1/2000 | O'Rourke | |
| 6,017,313 A | 1/2000 | Bratteli et al. | |
| 6,048,318 A | 4/2000 | Chesney et al. | |
| 6,071,244 A | 6/2000 | Band et al. | |
| 6,090,047 A | 7/2000 | Kass et al. | |
| 6,117,087 A | 9/2000 | Kamm et al. | |
| 6,141,590 A | 10/2000 | Renirie et al. | |
| 6,165,130 A | 12/2000 | Chio | |
| 6,216,094 B1 | 4/2001 | Fox Linton et al. | |
| 6,224,585 B1 | 5/2001 | Pfeiffer | |
| 6,228,033 B1 | 5/2001 | Kööbi et al. | |
| 6,231,498 B1 | 5/2001 | Pfeiffer et al. | |
| 6,270,461 B1 | 8/2001 | Chio | |
| 6,290,651 B1 | 9/2001 | Chesney et al. | |
| 6,315,735 B1 | 11/2001 | Joeken et al. | |
| 6,348,038 B1 | 2/2002 | Band et al. | |
| 6,394,958 B1 | 5/2002 | Bratteli et al. | |
| 6,471,655 B1 | 10/2002 | Baura | |
| 6,485,431 B1 | 11/2002 | Campbell | |
| 6,514,211 B1 | 2/2003 | Baura | |
| 6,554,774 B1 | 4/2003 | Miele | |
| 6,676,608 B1 | 1/2004 | Keren | |
| 7,220,230 B2 * | 5/2007 | Roteliuk et al. | 600/485 |
| 2002/0022785 A1 | 2/2002 | Romano | |
| 2002/0052553 A1 | 5/2002 | Shalman et al. | |
| 2003/0060722 A1 | 3/2003 | Pfeiffer et al. | |
| 2003/0167010 A1 * | 9/2003 | Pinsky | 600/485 |
| 2003/0191400 A1 | 10/2003 | Shalman et al. | |
| 2004/0087863 A1 | 5/2004 | Eide | |
| 2004/0158163 A1 | 8/2004 | Cohen et al. | |
| 2007/0191724 A1 * | 8/2007 | Hirsh | 600/523 |

FOREIGN PATENT DOCUMENTS

| | | | |
|---|---|---|---|
| EP | 420 085 A2 | 4/1991 | |
| EP | 448 979 A1 | 10/1991 | |
| EP | 564 492 B1 | 10/1993 | |
| EP | 569 506 B1 | 11/1993 | |
| EP | 642 760 A1 | 3/1995 | |
| EP | 947 160 A1 | 10/1999 | |
| EP | 947 941 A2 | 10/1999 | |
| EP | 1 236 435 B1 | 9/2002 | |
| WO | WO 90/03145 | 4/1990 | |
| WO | WO 90/11042 | 10/1990 | |
| WO | WO 92/06633 | 4/1992 | |
| WO | WO 92/11804 | 7/1992 | |
| WO | WO 92/12669 | 8/1992 | |
| WO | WO 94/14372 | 7/1994 | |
| WO | WO 94/22363 | 10/1994 | |
| WO | WO 95/16391 | 6/1995 | |
| WO | WO 97/24982 | 7/1997 | |
| WO | WO 98/19594 | 5/1998 | |
| WO | WO 99/02086 | 1/1999 | |
| WO | WO 00/64339 | 11/2000 | |

OTHER PUBLICATIONS

Fagard, R. and Conway, 3 (1990); "Measurement of cardiac output: Fick principle using catheterization"; Eur. Heart J. 11, Suppl. I, pp. 1-5.

Ganz, W. and Swan, H.J.C. (1972); "Measurement of blood flow by thermodilution"; Am. J. Cardiol. 29, pp. 241-246.

Goedje, O.; Hoeke, K.; Lichtwark-Aschoff, M.; Faltchauser, A.; Lamm, P.; Reichart, B.; "Continuous cardiac output by femoral arterial thermodilution calibrated pulse contour analysis: Comparison with pulmonary arterial thermodilution"; Critical Care Medicine, 27 (1999), 2407-2412.

Gratz, I; Kraidin, J.; Jacobi, A.G.; deCastro, N.G.; Spagna, P.; Larijani, G.E.; "Continuous noninvasive cardiac output as estimated from the pulse contour curve"; Journal of Clinical Monitoring, 8 (1992), 20-27.

Harms, M.P.M.; Wesseling, K.H.; Pott, F., et al. (1999); "Continuous stroke vol. monitoring by modelling flow from non invasive measurement of arterial pressure in humans under orthostatic"; Clin. Sci. 97, pp. 291-301.

Houtman, S.; Oeseburg, B. and Hopman, M.T.E. (1999); "Non invasive cardiac output assessment during moderate exercise: pulse contour compared with C02 rebreathing"; Clin. Physiol. 19, pp. 230-237.

Irlbeck, M.; Forst, H.; Briegel, J.; Haller, M.; Peter, K.; "Die kontinuierliche Messung des Herzzeitvolumens mit der Pulskonturanalyse; Der Anaesthesist"; 44 (1995), 493-500.

Jansen, J.R.; Wesseling, K.H.; Settels, J.J.; Schreuder, J.J.; "Continuous cardiac output monitoring by pulse contour during cardiac surgery"; European Heart Journal, 11 (1990), 26-32.

Jansen, J.R.C.; Schreuder, J.J.; Mulier, J.P.; Smith, N.T.; Settels, J.J. and Wesseling, K.H.; "A comparison of cardiac output derived from the arterial pressure wave against thermodilution in cardiac surgery patients"; British Journal of Anaesthesia, 87 (2) (2001), 212-22.

Jellema, W.T.; Wesseling, K.H.; Groeneveld, A.B.J; Stoutenbeek, C.P.; Thjis, L.G. and van Lieshout, J.J. (1999); "Continuous cardiac output in septic shock by simulating a model of the thermodilution"; Anesthesiology 90, pp. 1317-1328.

Jellema, W.T.; Imholz, B.P.M.; van Goudoever, J.; Wesseling, K.H. and van Lieshout, J.J. (1996); "Finger arterial versus intrabrachial pressure and continuous cardiac output during head up tilt testing in healthy subjects"; Clin. Sci. 91, pp. 193-200.

Langewouters, G.J.; Wesseling, K.H. and Goedhard, W.J.A. (1984); "The static elastic properties of 45 human thoracic and 20 abdominal aortas in vitro and the parameters of a new model"; J. Biomech. 17, pp. 425-435.

McKay, W.P.; Gregson, P.H.; McKay, B.W.; Militzer, J.; "Sternal acceleration ballistocardiography and arterial pressure wave analysis to determine stroke vol."; Clinical and Investigative Medicine, 22 (1999), 4-14.

Martin, J.F.; Volfson, L.B.; Kirzon-Zolin, V.V.; Schukin, V.G.; "Application of pattern recognition and image classification techniques to determine continuous cardiac output from the arterial pressure waveform"; IEEE Transactions on Biomedical Electronics, 41 (1994), 913-920.

Romano, Salvatore M.; Pistolesi, Massimo; "Assessment of cardiac output from systemic arterial pressure in humans"; Crit Care Med 2002 vol. 30, No. 8, pp. 1834-1841.

Sprangers, R.L.; Wesseling, K.H.; Imholz, A.L.; Imholz, B.P. and Wieling, W. (1991); "Initial blood pressure fall on stand up and exercise explained by changes in total peripheral resistance"; J. Appl. Physiol. 70, pp. 523-530.

Stok, W.J.; Baisch, F.; Hillebrecht, A.; Schulz, H. and Karemaker, J.M. (1993); "Noninvasive cardiac output measurement by arterial pulse analysis compared to inert gas rebreathing"; J. Appl. Physiol. 74, pp. 2687-2693.

Stok, W.J.; Stringer, R.C.O. and Karemaker, J.M. (1999); "Noninvasive cardiac output measurement in orthostasis: pulse contour analysis compared with acetylene rebreathing"; J. Appl. Physiol. 87, pp. 2266-2273.

Wesseling, K.H.; De Wit, B.; Weber, J.A.P. and Smith, N.T. (1983); "A simple device for the continuous measurement of cardiac output. Its model basis and experimental verification"; Adv. Cardiol. Phys. 5, Suppl. II, pp. 16 52.

Wesseling, K.H.; Jansen, J.R.C.; Settels, J.J. and Schreuder, J.J. (1993); "Computation of aortic flow from pressure in humans using a nonlinear, three element model"; J. Appl. Physiol. 74, pp. 2566-2573.

* cited by examiner

REAL-TIME MEASUREMENT OF VENTRICULAR STROKE VOLUME VARIATIONS BY CONTINUOUS ARTERIAL PULSE CONTOUR ANALYSIS

CROSS-REFERENCE TO RELATED APPLICATIONS

This application is a continuation-in-part of, claims priority of, and incorporates by reference U.S. patent application Ser. No. 10/728,705, filed 5 Dec. 2003 now U.S. Pat. No. 7,220,230, and Ser. No. 10/890,887, filed 14 Jul. 2004.

BACKGROUND OF THE INVENTION

1. Field of the Invention

This invention relates in general to cardiac monitoring and in particular to estimation of ventricular stroke volume variation (SVV) as well as to a system that implements the method.

2. Background Art

Stroke volume (SV), cardiac output (CO), etc., are important indicators not only for diagnosis of disease, but also for "real-time" monitoring of the condition of both human and animal subjects, including patients. Few hospitals are therefore without some form of equipment to monitor one or more of these cardiac parameters. Many techniques—invasive and non-invasive, as well as those that combine both—are in use and even more have been proposed in the literature.

Most of the techniques used to measure SV can usually be readily adapted to provide an estimate of CO as well, since CO is generally defined as SV times the heart rate HR, which is usually available to monitoring equipment. Conversely, most devices that estimate CO also estimate SV as a sub-step.

As is explained in greater detail below, still another cardiac parameter that promises to provide clinically important information is stroke volume variation SVV. One way to estimate SVV is simply to collect multiple SV values and calculate the differences from measurement interval to measurement interval.

One common way to measure SV or CO is to mount some flow-measuring device on a catheter, and then to thread the catheter into the subject and to maneuver it so that the device is in or near the subject's heart. Some such devices inject either a bolus of material or energy (usually heat) at an upstream position, such as in the right atrium, and determine flow based on the characteristics of the injected material or energy at a downstream position, such as in the pulmonary artery. Patents that disclose implementations of such invasive techniques (in particular, thermodilution) include:

U.S. Pat. No. 4,236,527 (Newbower et al., 2 Dec. 1980);
U.S. Pat. No. 4,507,974 (Yelderman, 2 Apr. 1985);
U.S. Pat. No. 5,146,414 (McKown, et al., 8 Sep. 1992); and
U.S. Pat. No. 5,687,733 (McKown, et al., 18 Nov. 1997).

Still other invasive devices are based on the known Fick technique, according to which CO is calculated as a function of oxygenation of arterial and mixed venous blood.

Invasive techniques have obvious disadvantages, the main one of which is of course that catheterization of the heart is potentially dangerous, especially considering that the subjects (especially intensive care patients) on which it is performed are often already in the hospital because of some actually or potentially serious condition. Invasive methods also have less obvious disadvantages: Some techniques such as thermodilution rely on assumptions, such as uniform dispersion of the injected heat, that affect the accuracy of the measurements depending on how well they are fulfilled. Moreover, the very introduction of an instrument into the blood flow may affect the value (for example, flow rate) that the instrument measures.

Doppler techniques, using invasive as well as non-invasive transducers, are also used to measure flow and to calculate SV and CO from the flow measurements. Not only are these systems typically expensive, but their accuracy depends on precise knowledge of the diameter and general geometry of the flow channel. Such precise knowledge is, however, seldom possible, especially under conditions where real-time monitoring is desired.

There has therefore been a long-standing need for some way of determining cardiac parameters such as SV, SVV, etc., that is both non-invasive, or at most minimally invasive, and accurate. One blood characteristic that has proven particularly promising for accurately determining such parameters with minimal or no invasion is blood pressure.

Most known blood-pressure-based systems rely on the so-called pulse contour method (PCM), which calculates an estimate of the cardiac parameter(s) of interest from characteristics of the beat-to-beat pressure waveform. In the PCM, "Windkessel" (German for "air chamber") parameters (characteristic impedance of the aorta, compliance, and total peripheral resistance) are typically used to construct a linear or non-linear, hemodynamic model of the aorta. In essence, blood flow is analogized to a flow of electrical current in a circuit in which an impedance is in series with a parallel-connected resistance and capacitance (compliance). The three required parameters of the model are usually determined either empirically, through a complex calibration process, or from compiled "anthropometric" data, that is, data about the age, sex, height, weight, etc., of other patients or test subjects. U.S. Pat. No. 5,400,793 (Wesseling, 28 Mar. 1995) and U.S. Pat. No. 5,535,753 (Petrucelli,.et al., 16 Jul. 1996) are representative of systems that rely on a Windkessel circuit model to determine CO.

PCM-based systems can monitor SV-derived cardiac parameters more or less continuously, with no need for a catheter (usually right heart) to be left in the patient. Indeed, some PCM systems operate using blood pressure measurements taken using a finger cuff. One drawback of PCM, however, is that it is no more accurate than the rather simple, three-parameter model from which it is derived; in general, a model of a much higher order would be needed to faithfully account for other phenomena, such as the complex pattern of pressure wave reflections due to multiple impedance mismatches caused by, for example, arterial branching. Because the accuracy of the basic model is usually not good enough, many improvements have been proposed, with varying degrees of complexity The "Method and apparatus for measuring cardiac output" disclosed by Salvatore Romano in U.S. Published Patent Application 20020022785 A1 (21 Feb. 2002, "Method and apparatus for measuring cardiac output") represents a different attempt to improve upon PCM techniques by estimating SV, either invasively or non-invasively, as a function of the ratio between the area under the entire pressure curve and a linear combination of various components of impedance. In attempting to account for pressure reflections, the Romano system relies not only on accurate estimates of inherently noisy derivatives of the pressure function, but also on a series of empirically determined, numerical adjustments to a mean pressure value.

Fluid administration in hemodynamically unstable patients is often a major challenge when it-comes to measuring SV, CO, or other hemodynamic parameters in real time. Correct clinical assessment of hypovolemia is difficult, as is the decision to undertake fluid resuscitation as the initial treatment strategy. Specifically, it is very difficult to predict whether a hemodynamically unstable patient will respond to fluid therapy with an increase in stroke volume and cardiac output. Moreover, fluid overload can cause significant pulmonary or cardiac dysfunction, whereas fluid insufficiency may cause tissue damage resulting in vital organ dysfunction. A patient's fluid responsiveness is the major and most important determinant to assess the adequacy of fluid resuscitation therapy and to ensure optimal cardiac performance and organ perfusion.

Many bedside indicators of ventricular preload have been used as predictors of fluid responsiveness. Right arterial pressure (RAP) and pulmonary artery occlusion pressure (PAOP) are the most commonly used in the intensive care unit (ICU) when deciding to administer fluids. Other bedside indicators of ventricular preload include right ventricular end diastolic volume (RVEDV) and left ventricular end diastolic area (LVEDA) measured with transesophageal echocardiography. Several studies and case reports have shown, however, that these static indicators based on cardiac filling pressures have poor predictive value and often fail to give adequate information about fluid responsiveness.

Recently, several studies have confirmed the clinical significance of monitoring the variations observed in left ventricular stroke volume that result from the interaction of the cardiovascular system and the lungs under mechanical ventilation. These stroke volume variations (SVV) are caused by the cyclic increases and decreases in the intrathoracic pressure due to the mechanical ventilation, which lead to variations in the cardiac preload and afterload. SVV has recently been extensively investigated and several studies have shown the usefulness of using SVV as predictor of fluid responsiveness in various clinical situations. Several other parameters based on SVV have been found to be useful as well. In particular, systolic pressure variation (SPV) with its delta-Up ($\Delta$Up) and delta-Down ($\Delta$Down) components has been found to be a very useful predictor of fluid responsiveness. SPV is based on the changes in the arterial pulse pressure due to respiration-induced variations in stroke volume. Yet another parameter that has recently been investigated and shown to be a valid indicator of fluid responsiveness is the pulse pressure variation (PPV).

Recent developments in arterial pulse contour analysis methods have opened unique opportunities for less-invasive, continuous and real-time estimation of SVV. This allows clinicians to use SVV routinely along with SV and CO in their assessment of the hemodynamic state of critical care patients.

Existing systems for measuring fluid responsiveness based on respiration-induced changes in the arterial pulse pressure are almost all based on one of only a few methods. Some of the methods described in the literature include the following measurement of Pulse Pressure Variation (PPV), Systolic Pressure Variation (SPV) and Stroke Volume Variation (SVV).

PPV estimation is based on some version of the following Equation 1:

$$PPV=100 \cdot [PP_{max}-PP_{min}]/[\tfrac{1}{2}(PP_{max}+PP_{min})] \qquad \text{(Equation 1)}$$

where PP is measured pulse pressure, $PP_{max}$ and $PP_{min}$ are, respectively, the maximum and the minimum peak-to-peak values of the pulse pressure during one respiratory (inspiration-expiration) cycle.

SPV estimation is based on some version of the following Equation 2:

$$SPV=100 \cdot [SP_{max}-SP_{min}]/[\tfrac{1}{2}(SP_{max}+SP_{min})] \qquad \text{(Equation 2)}$$

where SP is measured systolic pressure, $SP_{max}$ and $SP_{min}$ are respectively the maximum and minimum values of the systolic pressure during one respiratory cycle.

Similarly, SVV estimation is based on some version of the following Equation 3:

$$SVV=100 \cdot [SV_{max}-SV_{min}]/[\tfrac{1}{2}(SV_{max}+SV_{min})] \qquad \text{(Equation 3)}$$

where SV is stroke volume, $SV_{max}$ and $SV_{min}$ are respectively the maximum and minimum values of the stroke volume during one respiratory cycle.

In Equations 1, 2, and 3, the denominators are the averages of the maximum and minimum values of PP, SP and SV, respectively. In other words, the denominators are mean values, albeit of only two measurement points. This simple averaging of extreme values has been most common merely to simplify the calculations, which have typically been performed by hand. More reliable values may be obtained, however, by using the mean of all the measurement values over the measurement interval, that is, the first statistical moment of PP, SP, and SV.

Thus, for each of PPV, SPV and SVV, the respective variation value formula expresses the magnitude of the range of the value (maximum minus minimum) relative to the mean of the extreme (maximum and minimum) values.

The specific monitoring of SVV has both specific difficulties and advantages. Physiologically, SVV is based on several complex mechanisms of cardio-respiratory interaction. In brief: mechanical ventilation causes changes in left ventricular preload, which leads to distinct variations in left ventricular stroke volume and systolic arterial pressure. Monitoring of SVV enables prediction of left ventricular response to volume administration and helps with correct assessment of hypovolemia and the subsequent decision to undertake volume resuscitation in many critical situations.

In addition to the three methods listed above, there is a fourth method, known as Perel's method, which is generally called the "respiratory systolic variation test." This method involves airway pressure maneuvers, such as inducing tidal volumes of varying amplitudes preceded by a short apnea period. U.S. Pat. No. 5,769,082 (Perel) describes this method. Because of the requirement for pressure maneuvers, this method is not suitable for real-time monitoring.

The methods listed above are implemented in some CO monitoring instruments such as LiDCO Ltd.'s cardiac monitor and the PiCCO system of Pulsion Medical Systems (see, for example, U.S. Pat. No. 6,315,735—Joeken et al), both of which rely on Equation 3. Tests by the inventors show however, that these methods are so noisy that they do not allow for accurate real-time monitoring of the respiration-induced changes in the arterial pulse pressure. The main reason for the noise problems in the SVV estimation in those instruments is the way SV is calculated. For example, the PiCCO system uses a beat-to-beat stroke volume estimation method based on a pulse contour algorithm that involves detection of specific points in the blood pressure waveform, such as the dicrotic notch. Precise detection of the dicrotic notch and other points in the blood pressure signal, however, is difficult, due to the inconstancy of the blood pressure waveform and its volatile nature.

What is needed is therefore a system and method of operation for estimating SVV in real time more accurately and robustly than is now possible, using at most minimally invasive techniques. This invention meets this need.

SUMMARY OF THE INVENTION

The invention provides a method and related system implementation for determining a cardiac parameter equal to or derivable from cardiac stroke volume variation (SVV): A waveform data set corresponding to arterial blood pressure, determined either invasively or non-invasively, is determined and input to a processing system over a computation interval that covers at least two cardiac cycles; a standard deviation value for the waveform data set is then calculated over each cardiac cycle; and an estimate of the SVV is calculated as a function of the standard deviation values.

Different methods may be used to calculate the values used in the SVV estimation. For example, maximum and minimum standard deviation values over the computation interval may be determined, and the estimate of the SVV can then be calculated as a function of the maximum and minimum standard deviation values. A mean standard deviation value is preferably also computed over the computation interval and the estimate of the SVV can then be calculated to be proportional to the difference between the maximum and minimum standard deviation values relative to the mean standard deviation value. As one alternative, the processing system may compute the standard deviation of the standard deviation values over the computation interval and then estimate the SVV as being proportional to the ratio between the standard deviation of the standard deviation values and the mean of the standard deviation values.

Blood pressure may be measured either invasively or non-invasively, for example by using a catheter-mounted pressure transducer or a finger cuff. The measured arterial pressure is then converted into the waveform data set.

The inventors have also found that the above-described method according to the invention may also be used to calculate an estimate of right ventricular end diastolic volume, which is inversely proportional to the calculated estimate of the cardiac stroke volume variation.

According to one feature of the invention that has been found to be advantageous, an approximating function is computed that best matches the calculated standard deviation values according to a predetermined metric over at least one of the computation intervals. The approximating function is then sampled at an interval-specific sampling rate to create a set of sampled, approximating values, which are then low-pass filtered before the estimate of the SVV is computed from them.

This method of approximating, resampling and low-pass filtering with an adjustable rate may be extended for use in estimating other cardiac or hemodynamic parameters than SVV, for example, systolic pressure variation, pulse pressure variation, etc. In this case, the waveform data set is generated and input to the processing system to correspond to whatever measurement parameter is selected. A series of measurement values is then generated from the waveform data set; an approximating function is computed that best matches the measurement values (or some function of them) according to a predetermined metric; over each of at least one computation interval, a set of sampled, approximating values is then created by sampling the approximating function at an interval-specific sampling rate; the sampled, approximating values are then low-pass filtered; and an estimate of the output value is then computed as a function of the low-pass filtered, sampled approximating values.

DETAILED DESCRIPTION

Introduction

In broadest terms, the invention involves the beat-to-beat of stroke volume variation SVV as a function of the standard deviation of the blood pressure waveform over a plurality of cardiac cycles. Of course, the invention may be used to determine any other cardiac parameter that can be derived from SVV.

The invention may be used to advantage with any type of subject, whether human or animal. Because it is anticipated that the most common use of the invention will be on humans in a diagnostic setting, the invention is described below primarily in use with a "patient." This is by way of example only, however—it is intended that the term "patient" should encompass all subjects, both human and animal, regardless of setting.

Because of its clinical significance, it is anticipated that most implementations of the invention will generate SVV estimates based on measurements of systemic arterial blood pressure. It would also be possible to use measurements of blood pressure taken elsewhere, however, such as in the pulmonary artery on right side, although such sites may require invasive intracardiac measurement.

Pressure Waveforms

Figure 1:
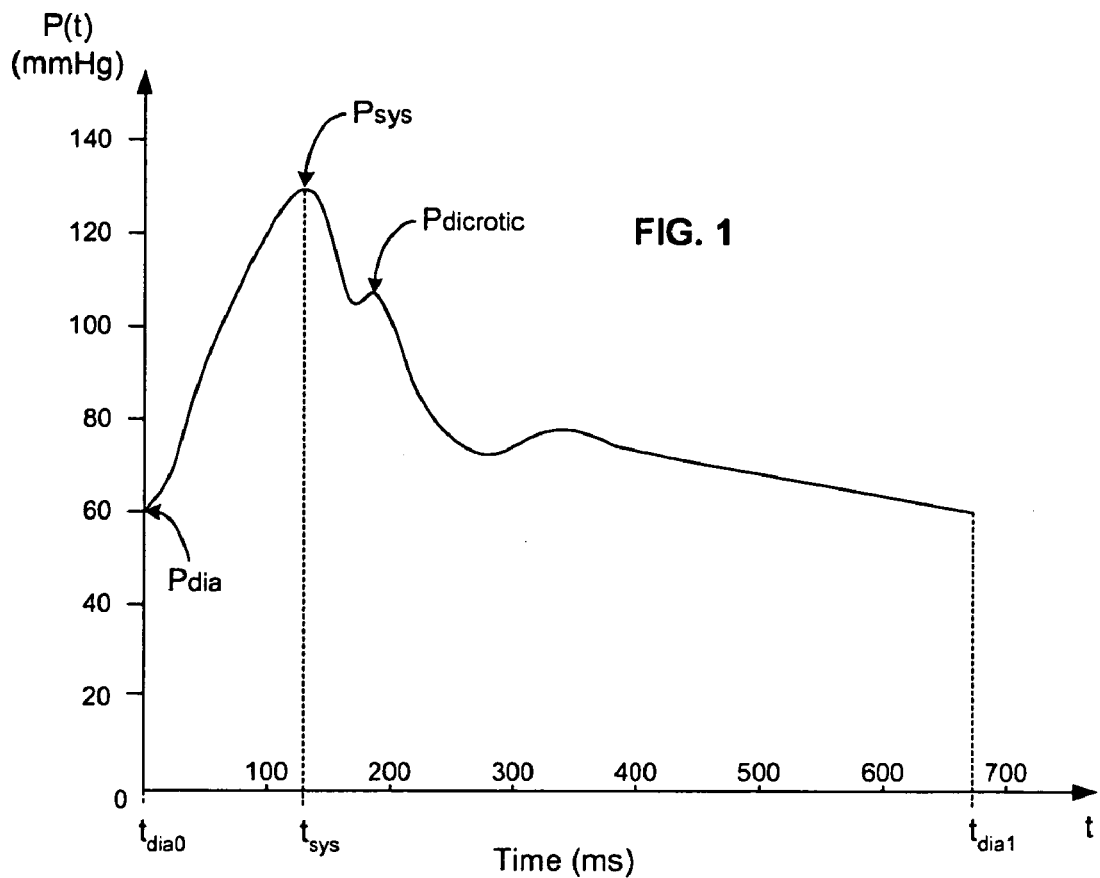
FIG. 1 is an illustrative example of a complex blood pressure curve over one beat-to-beat heart cycle.

FIG. 1 illustrates an example of a waveform P(t) of arterial pressure taken over a single heart cycle, here, from the point of diastolic pressure $P_{dia}$ at time $t_{dia0}$, through the time $t_{sys}$ of systolic pressure $P_{sys}$, to a time $t_{dia1}$ at which the blood pressure once again reaches $P_{dia}$.

According to the invention, P(t), or any signal that is proportional to P(t), may be measured at any point in the arterial tree, either invasively or non-invasively. If invasive instruments are used, in particular, catheter-mounted pressure transducers, then any artery may be used as a measurement point. Placement of non-invasive transducers will typically be dictated by the instruments themselves—the placement of finger cuffs, upper arm pressure cuffs, and earlobe clamps should be obvious. Regardless of the instrument, it will ultimately produce, or cause to be produced, an electric signal corresponding (for example, proportional) to P(t).

Rather than measure arterial blood pressure directly, any other input signal may be used that is proportional to blood pressure. Any needed scaling or conversion may then be done at any or all of several points in the calculations described below. For example, if some signal other than arterial blood pressure itself is used as input, then it may be calibrated to blood pressure before its values are used in the computations described below. In short, the fact that the invention may in some cases use a different input signal than a direct measurement of arterial blood pressure does not limit its ability to generate an accurate SVV estimates. The only requirement of this invention is that a signal or data set equal or at least having a known relationship to (such as being proportional to) the patient's blood pressure over the interval of interest (including continuously) must be made available to the processing system (see below) that carries out the signal conditioning and various calculations described below.

Figure 2:
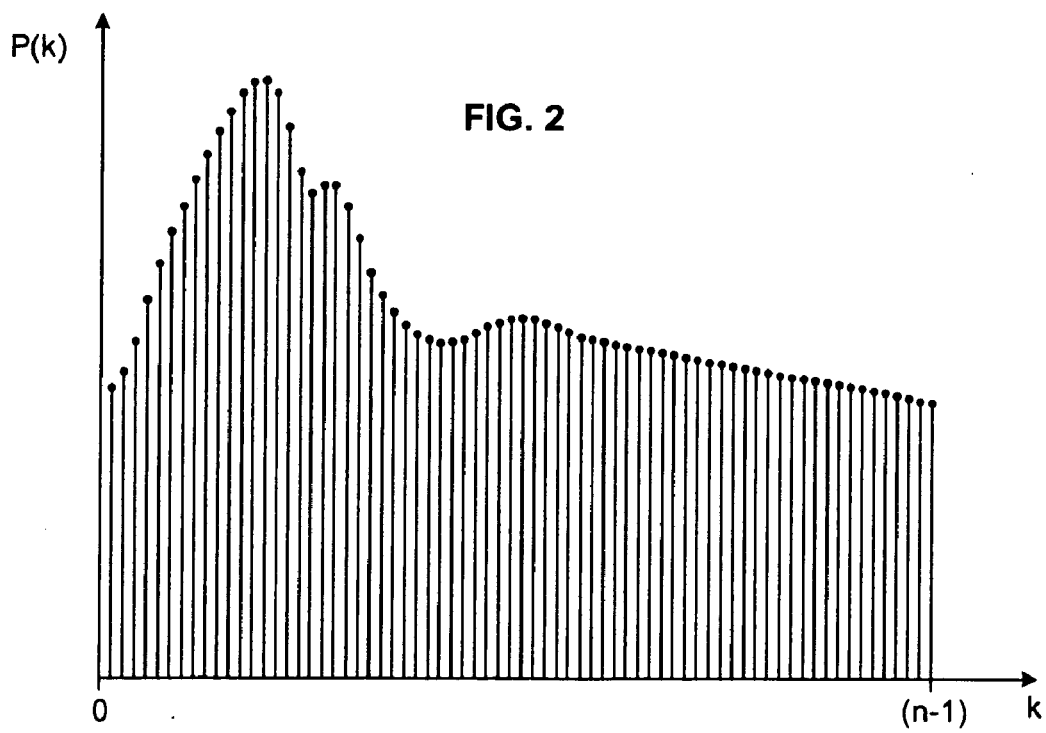
FIG. 2 illustrates a discrete-time representation of the pressure waveform in FIG. 1.

As is well known, and as is illustrated in FIG. 2, analog signals such as P(t) can be digitized into a sequence of digital values using any standard analog-to-digital converter (ADC). In other words, P(t), $t0 \leq t \leq tf$, can be converted, using known methods and circuitry, into the digital form P(k), k=0, (n−1), where t0 and tf are initial and final times, respectively, of the computation interval and n is the number of samples of P(t) to be included in the calculations, distributed usually evenly over the computation interval.

Standard Deviation

The calculation of the mean and standard deviation of a continuous or discrete function or data set f is a very well known procedure, and is usually indicated in references by the Greek letters $\mu$ and $\sigma$, respectively, or, in most programming languages, by function names such as mean and std. Thus, $\mu(f)$ and mean(f) represent the mean of the function or data set f over some interval and $\sigma(f)$ and std(f) represent its standard deviation.

Now consider the calculation of the mean and standard deviation of a series of blood pressure values P=P(k) over some interval such as k=1, ..., n. The most common way to calculate the mean $\mu(P)$ and standard deviation $\sigma(P)$ is to use the algorithms familiar to all who have taken even an introductory course in Statistics:

$$\mu(P) = \text{mean}(P) = 1/m \cdot \text{SUM}[P(k)] \quad \text{(Equation 4)}$$

$$\sigma(P) = \text{std}(P) = \text{sqrt}\{1/(m-1) \cdot \text{SUM}[P(i) - \mu(P)]^2\} \quad \text{(Equation 5)}$$

where sqrt indicates the square root and SUM indicates summation over the interval i=0, ..., (m−1). Note that the discrete-value formulas for variance (the square of standard deviation) usually scale by 1/(m−1) instead of 1/m for well-known statistical reasons.

As will become clearer below, the invention generates a robust estimate of SVV in real time from calculations of the standard deviation of the pressure waveforms, preferably over several cardiac cycles. Although the standard "textbook" formula for standard deviation (Equation 5) is preferred for well known statistical reasons, any formula or algorithm that provides an acceptably accurate value of or corresponding to standard deviation may be used instead in the invention. For example, at least in the context of blood pressure-based measurements, a rough approximation to $\sigma(P)$ can be had by dividing by three the difference between the maximum and minimum measured pressure values. Moreover, the maximum, or absolute value of the minimum, of the first derivative of the P(t) with respect to time is generally proportional to $\sigma(P)$.

In this discussion of the invention are several references to calculations using "pressure" values and "standard deviation" values. In the preferred embodiment of the invention, these are in fact direct measurements of blood pressure, in particular arterial blood pressure, and standard deviation as computed using the most common formula, given above as Equation 5. It is to be understood, however, that "pressure" may equally refer to indirect measurements, or measurements of some physiological characteristic that correlates or corresponds to or can be otherwise related to pressure. Similarly, "standard deviation" may also refer to any value known to approximate the value that would be given by the usual formula; examples of such alternatives are given in the previous paragraph.

SVV Computation

The standard formula for calculating cardiac output (CO) is CO=SV·HR, which simply expresses relationship that the amount of blood the heart pumps per minute is equal to how much it pumps per cycle (SV) times the number of cycles in a minute. Given HR, the problem, of course, is that this assumes a constant value of SV, or knowledge of the mean SV. Based on the observation that the pulsatility of a pressure waveform is created by the cardiac stroke volume into the arterial tree, one of the present inventors earlier discovered that SV can be approximated as being proportional to the standard deviation of the arterial pressure waveform P(t), or of some other signal that itself is proportional to P(t). Thus, one way to estimate SV is to apply the relationship $$SV = K \cdot \sigma(P) = K \cdot \text{std}(P) \quad \text{(Equation 6)}$$

where K is a calibration constant and from which follows:

$$CO = K \cdot \sigma(P) \cdot HR = K \cdot \text{std}(P) \cdot HR \quad \text{(Equation 7)}$$

Substituting Equation 6 into Equation 3 yields a formula for SVV that is a function of std(P):

$$SVV = 100 \cdot [\text{std}(P)_{max} - \text{std}(P)_{min}] / [\tfrac{1}{2}(\text{std}(P)_{max} + \text{std}(P)_{min})] \quad \text{(Equation 8)}$$

where $\text{std}(P)_{max}$ and $\text{std}(P)_{min}$ are, respectively, the maximum and minimum values of the standard deviation of the pressure waveform over a computation interval. In the preferred embodiment of the invention, this computation interval is a respiratory cycle.

As mentioned above, using the statistical mean of pressure—mean(P)—in the denominator over the measurement interval will generally provide more accurate and robust estimates than using the mean only of the maximum and minimum values, although the invention may use either mean in the denominator. The preferred form of Equation 8 is thus:

$$SVV = 100 \cdot [\text{std}(P)_{max} - \text{std}(P)_{min}] / \text{mean}(\text{std}(P)) \quad \text{(Equation 9)}$$

where mean(std(P)) is the mean of the standard deviation of the pressure waveform, not the mean $\mu(P)$ of the pressure waveform itself, although this parameter will be included in the calculation of any std(P) value. Also, depending on the type of signal conditioning and conversion methods (see below) used to condition the measured pressure signal P(t) and then to convert it into discrete form, it may be necessary or desirable to scale Equation 9. It will be obvious to any skilled system designer whether scaling is needed, and how to do so; for that reason, any scaling factor is not shown in Equation 9 but can be assumed.

Figure 3:
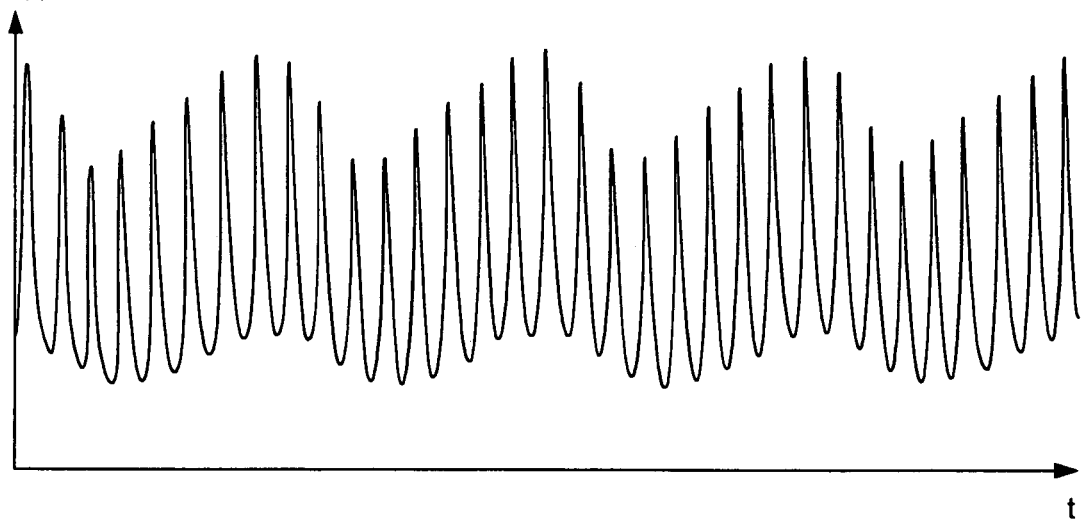
FIG. 3 illustrates a series of blood pressure signals (waveforms) over different respiratory cycles.

FIG. 3 illustrates a sequence of measured or otherwise acquired arterial pressure waveforms over approximately three respiratory cycles. In practice, the sequence will be a data set P(k) derived from a sampled measurement of arterial pressure P(t). As mentioned above, the P(k) values may be obtained through direct, invasive or non-invasive measurement, or may be input from some other source, such as from a remote monitor or even a pre-recorded data set, although this latter possibility would of course not provide real-time monitoring and would in most cases be sued primarily for comparison or experimentation.

Figure 4:
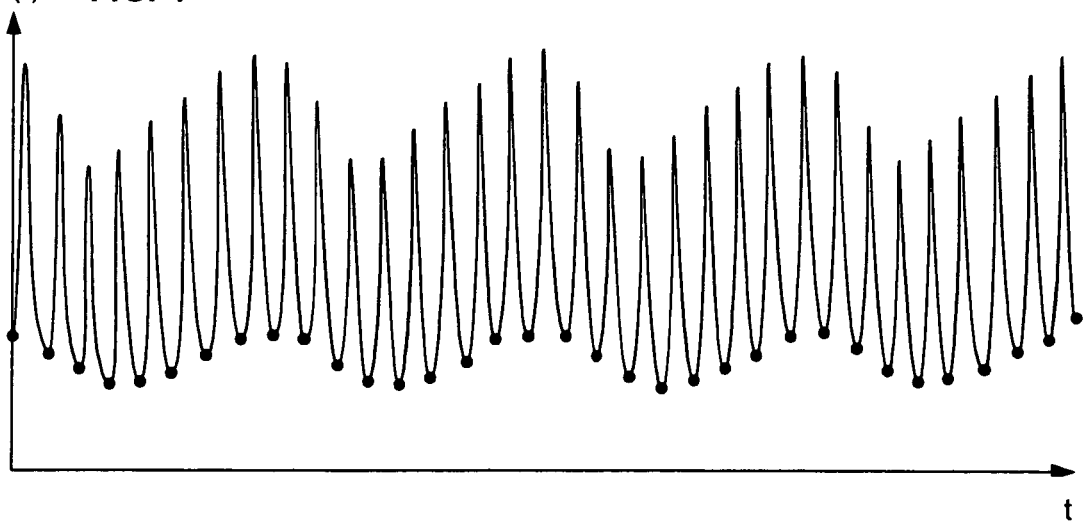
FIG. 4 illustrates beat-to-beat detection in the waveform of FIG. 3, that is, the isolation of individual pressure waveforms per cardiac cycle.

In FIG. 4, dots are included in the waveform of FIG. 3 to indicate the beginning of each cardiac cycle (that is, each "beat") over the illustrated computation interval. The beginning of each cardiac cycle may be determined in any of a number of known ways using any known system that is or includes a heart rate monitor. Assuming, for example, as is often the case, that the patient's cardiac electrical activity is also being monitored by an electrocardiogram system (EKG), then the beginning of each cardiac cycle may be determined to occur at the sampled pressure value immediately following each R-wave. Pressure-based, pulse-rate monitors may also be used and are in fact preferred because they will then be better synchronized with the blood pressure signal than will, for example, an EKG signal.

If no such external device is present, then the beginning of each cardiac cycle can also be determined using software alone from the pressure waveform P(k) itself, for example, simply by assuming that each beat begins at the time of minimum (diastolic) pressure $P_{dia}$ (see FIG. 1), or by using Fourier transformation or derivative analysis. In these cases, the heart rate "monitor" is a software construct. In such case, care should be taken, using known techniques, to ensure that a local pressure minimum is not caused by respiration itself, but is in fact at the diastolic time.

Figure 5:
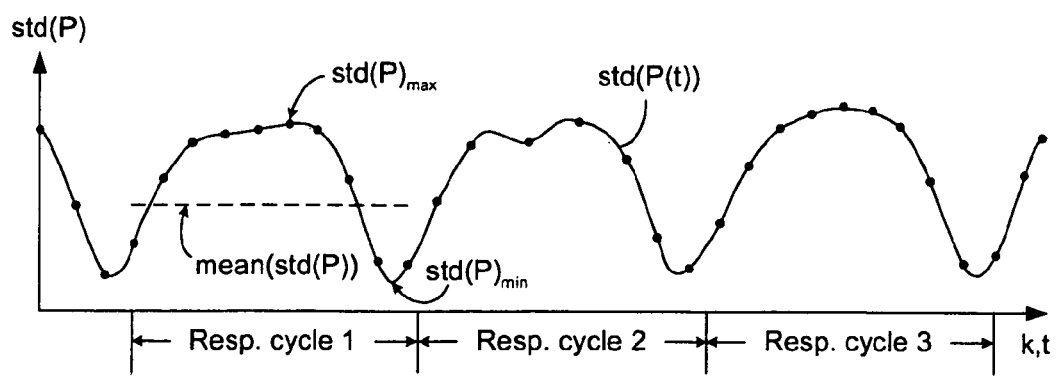
FIG. 5 illustrates a pressure standard deviation curve.

Let P(k,i) be the i'th beat-to-beat arterial pressure signal in a computation interval. The standard deviation std(P(k,i)) can then be computed as described above and will be a single-value (scalar) result. The standard deviation values for each of the beat-to-beat arterial pressure signals in the computation interval can be similarly computed. In FIG. 5, each dot on a standard deviation curve std(P(t)) indicates the computed standard deviation value for one beat-to-beat arterial pressure signal.

Computation of SVV according to Equation 9 requires the maximum, minimum and mean values of std(P(k,i)) for each computation interval. One way to get $std(P)_{max}$ and $std(P)_{min}$ for a given-respiratory cycle (roughly three respiratory cycles are illustrated in FIG. 5) is simply to take the greatest and least of the discrete std(P(k,i)) values in the cycle. These can be identified rapidly by simple scanning of the computed values.

During actual monitoring, noise and other factors may cause one or more std(P(k,i)) values to become unreliable. Deviant and potentially unreliable std(P(k,i)) values can be detected using known algorithms, such as those based on pattern-matching. Interpolation can then be used to determine replacements for the excluded value(s). A preferred method for smoothing and filtering measured values to increase reliability—applicable even in determinations of other cardiac and hemodynamic parameters than SVV—is described below.

Any standard algorithm may be used to identify $std(P)_{max}$ and $std(P)_{min}$ from std(P(k,i)). The simplest method is to take the greatest and least measured values. Alternatively, the measured std(P(k,i)) points may be used as the basis for determining an approximating or smoothing function (for example, using splines or polynomials); this would in many cases allow for identification of extreme std(P(t)) values that lie between the computed values, such as $std(P)_{min}$ shown in FIG. 5. The values mean(std(P(k,i))=mean(std(P)) can be calculated using the standard statistical formula (see, Equation 4). FIG. 5 also illustrates the value of mean(std(P)) for the first respiratory cycle. Once $std(P)_{max}$ and $std(P)_{min}$ are determined for a given respiratory cycle, then an SVV value for that respiratory cycle can be readily computed according to either Equation 8 or Equation 9. Assuming the preferred case that mean(std(P(k)) is also computed then a more accurate and robust SVV can be computed using Equation 9. The computed value(s) of SVV may then be displayed for the user, stored, transmitted, and/or used in further calculations in any desired way.

As mentioned above, the preferred computation interval is one respiratory cycle. The beginning and end times of these cycles may be detected using any known device. Note that many patients who would need this invention will also be ventilated, in which case the ventilator itself may provided the needed timing signals for the invention to separate the different respiratory cycles.

As illustrated in FIGS. 3 and 4, however, it would also be possible to detect the boundaries of respiratory cycles by analyzing the suite of acquired pressure waveforms itself: The times of the least diastolic pressures (the local minima of the "envelope" of the pressure waveforms) will normally also mark the beginning of a respiratory cycle. In some situations, however, such a software-based detection method could be less precise than simply receiving a signal from another system that specifically includes respiratory monitoring, especially where the patient's breathing is weak.

Computation Interval—Alternative SVV Computation

Above, it is assumed that an SVV value is estimated for each respiratory cycle. This is not necessary. Rather, it would also be possible to use the same methodology and equations described above to compute a single SVV value over a computation interval greater than one respiratory cycle, even over the entire time of a monitoring session. Although this would of course not show cycle-to-cycle SVV trends, it may provide more accurate results for each monitoring session and thus better indication of more long-term (such as session-to-session or day-to-day) trends. It is not necessary always to compute over "extremes" intervals, however. Rather, an SVV value could be computed for any n-cycle time periods, with n ranging from one (the case described above) upward.

Assume, for example, that a computation period is greater than one respiratory cycle. For the sake of illustration, assume that all three respiratory cycles shown in FIG. 5 are to constitute a single, combined computation interval. Even in this case, there will be a set std(P(k,i)) of computed std(P(k)) values (the "points" on the curve), indeed, even more values. These standard deviation values will themselves have a standard deviation and mean (mid-point between extreme values). According to an alternative embodiment of the invention, useful for computation intervals spanning more than one respiratory cycle, SVV is estimated thus:

$$SVV = C \cdot 100 \cdot std(std(P(k,i))/mean(std(P(k,i)) \quad \text{(Equation 10)}$$

where C is an empirically determined scaling constant. In one test of the invention, the inventors determined C to be approximately 2.7, regardless of the number of respiratory cycles included in the computation interval; normal experimental methods may be used to determine C in any given implementation of the invention.

This alternative, multi-cycle method does not require the system to determine any $std(P)_{max}$ or $std(P)_{min}$ values. Consequently, it is not even advantageous to determine an interpolating, approximating function for the std(P(k)) values over the computation interval.

Optional Smoothing, Resampling and Filtering

Figure 6:
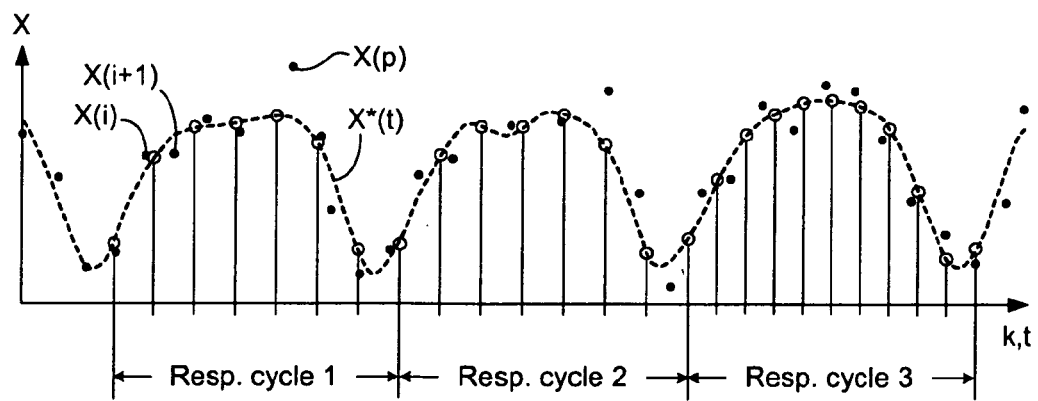
FIG. 6 illustrates optional digital pre-processing involving smoothing and filtering of discrete cardiac or hemodynamic measurement values.

See FIG. 6, in which a sequence of measurement values X(k) of a cardiac or hemodynamic value X is plotted as dots. In the embodiment of the invention described above, X(k) is std(P(k)), with one measurement value per cardiac cycle. The optional digital pre-processing described here is, however, also applicable to any other cardiac or hemodynamic value, such as systolic or pulse pressure, or even a non-pressure related parameter such as blood velocity measurements obtained from Doppler ultrasound scanning.

The measurement values will seldom fall neatly on a well-defined profile, since the underlying parameter is affected not only by noise, but also by natural irregularities such as a non-constant heart rate, different respiration patterns, etc. In many cases, the measurement system may itself be able to warn of, identify and exclude unreliable measurement values. For example, if signal strength falls below some predetermined minimum, then the values of the parameter measured during such time may be tagged or excluded. In other cases, unreliable values may be undetectable without further analysis. In FIG. 6, for example, the measurement point marked X(p) deviates so much from the apparent pattern that it could reasonably be assumed to be unreliable.

As mentioned above, one way to identify deviant values is by using pattern matching, in which the measured points are compared with one or more pre-stored templates, obtained from controlled studies done for a patient population, or simply verified profiles measured in the same patient. Any point that deviates from the template(s) by more than some threshold amount, measured in any known manner, can then be excluded.

In the preferred embodiment of the invention, for each computation interval, an approximating function (which may be the concatenation or combination of more than one partial function) is generated so as to create an interval profile that best matches the measured points according to any known metric, that is, in any known sense, such as least squares. For example, polynomial functions such as splines (two examples: B-splines and Bezier curves), reduced-component Fourier representations, etc., may be quickly calculated to generate an appropriate approximating function. In FIG. 6, the approximating function for the first respiratory interval is labeled X*(t).

In the illustrated examples, the computation interval is a respiratory cycle. Other intervals may be chosen depending on the parameter of interest, and need not necessarily be related to the respiratory cycles at all. Even for those that do, it is not necessary for the measurement interval to be a single cycle, or a whole multiple of single cycles, although this will in general make the most sense where the parameter of interest is affected by respiration and will also generally simplify calculations.

Once the approximating function is computed, the preferred embodiment of the invention low-pass filters the values per computation interval. The theory and implementation of digital low-pass filters is well known. Some set of sampled values are used as inputs to an algorithm that calculates some weighted linear or rational function of them to produce a transformed, filtered set of output values. Typical digital filters generally assume a constant "distance" between samples, however, and most such filters also have fixed coefficients.

According to this aspect of the invention, however, the input values to the low-pass filter are obtained by sampling the approximating function—possibly (but not necessarily) even at a higher rate than the rate at which the actual measurement values were obtained. In FIG. 6, the sample points are indicated by open dots on the approximating curve X*(t). The sample points of the approximating curve X*(t) are then input to a digital low-pass filter, whose cut-off frequency may be chosen in any known manner, and will depend on the known nature of the hemodynamic or cardiac parameter that is to be estimated, as well as of the measurement values X(k).

Once the desired cut-off frequency is determined, then the coefficients of a suitable low-pass filter may be determined in any known manner.

Note that this procedure enables even spacing of the sample points, even though, because of a changing heart rate, for example, the actual measured values may not be evenly spaced. Moreover, note that the sampling rate for respiratory cycle (here chosen as the computation interval) 3 is greater than that for cycles 1 and 2. One way to select the sampling rate for each given computation interval is to choose as many evenly spaced samples of the approximating curve X*(t) as there are actual measurement values in the computation interval. This is not necessary, however, but rather the sampling rate may be chosen as desired, for example, to satisfy the Nyquist criterion and reduce aliasing effects for the type of digital low-pass filter used.

Tests by the inventors have shown that these steps of smoothing (via the approximating function), re-sampling (that is, sampling that occurs after that performed for the analog-to-digital conversion), and adjustable-coefficient low-pass filtering, improve the ability of the invention to reject noise and produce more reliable SVV values. As mentioned above, the procedure may also be used for other estimated parameters than SVV.

System Components

Figure 7:
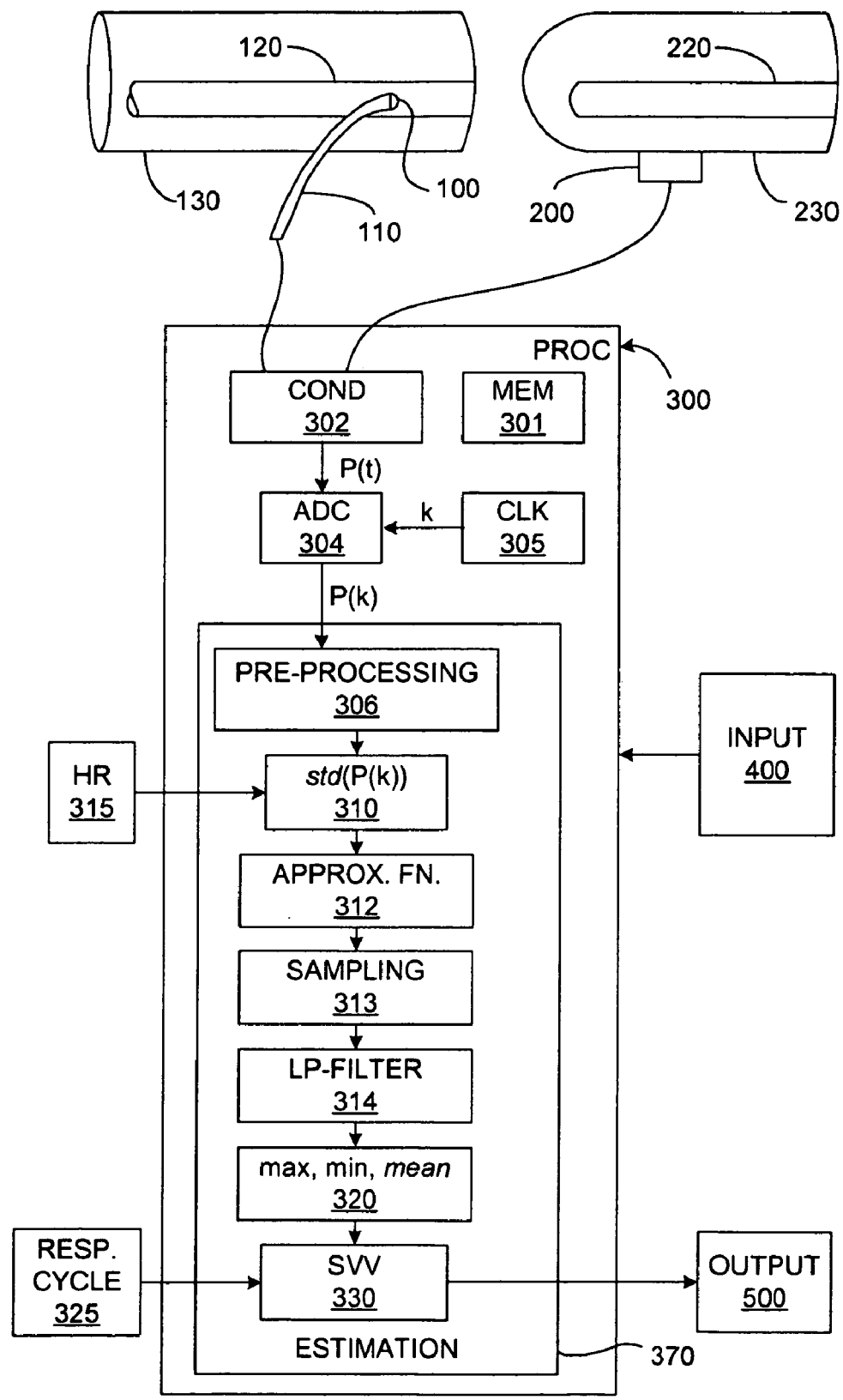
FIG. 7 is a block diagram showing the main components of a system according to the invention.

FIG. 7 shows the main components of a system that implements the method described above for sensing pressure and calculating SVV according to the invention. The invention may be included within an existing patient-monitoring device, or it may be implemented as a dedicated monitor. As is mentioned above, pressure, or some other input signal proportional to pressure, may be sensed in either or, indeed, both, of two ways: invasively and non-invasively. Simply because it is anticipated to be the most common implementation of the invention, the system is described as measuring arterial blood pressure as opposed to some other input signal that is converted to pressure.

FIG. 7 shows both types of pressure sensing for the sake of conciseness; in most practical applications of the invention, either one or several variations will typically be implemented. In invasive applications of the invention, a conventional pressure sensor 100 is mounted on a catheter 110, which is inserted in an artery 120 of a portion 130 of the body of a human or animal patient. Such artery could be an ascending aorta, or pulmonary artery, or, in order to reduce the level of invasiveness, the artery 120 could be peripheral, such as the femoral, radial or brachial artery. In the non-invasive applications of the invention, a conventional pressure sensor 200, such as a photo-plethysmographic blood pressure probe, is mounted externally in any conventional manner, for example using a cuff around a finger 230 or a transducer mounted on the wrist of the patient. FIG. 3 schematically shows both types.

The signals from the sensors 100, 200 are passed via any known connectors as inputs to a processing system 300, which includes one or more processors and other supporting hardware, such as a memory 301, and system software (not shown) usually included to process signals and execute code. The invention may be implemented using a modified, standard, personal computer, or it may be incorporated into a larger, specialized monitoring system. In this invention, the processing system 300 also may include, or is connected to, conditioning circuitry 302 which performs such normal signal processing tasks as amplification, filtering, ranging, etc., as needed.

The conditioned, sensed input pressure signal P(t) is then converted to digital form by a conventional analog-to-digital converter ADC 304, which has or takes its time reference from a clock circuit 305. As is well understood, the sampling frequency of the ADC 304 should be chosen with regard to the Nyquist criterion so as to avoid aliasing of the pressure signal; this procedure is very well known in the art of digital signal processing. The output from the ADC 304 will be the discrete pressure signal P(k), whose values may be stored in conventional memory circuitry (not shown).

A signal pre-processing module 306 is preferably included, with routines to provide such known pre-processing as digital filtering for general (as opposed to interval-to-interval) noise removal, for motion artifact rejection, pulse beat detection (if needed), for rejection of bad beats, etc. This module may also be implemented wholly or partially in hardware. As mentioned above, known circuitry may be included to indicate, for example, that signal strength is too low, and that the delivered measurement values are unreliable. As such, the module 306 may also be located functionally, wholly or partially, before the ADC 304.

The values P(k) are passed (usually, accessed from memory by) to a software module 310 comprising computer-executable code for computing the standard deviation of P(k) over a computation interval such as a cardiac cycle, which may be _ triggered by any known device or software routine 315 that detects heart rate or at least signals the beginning of a cardiac cycle. Even moderately skilled programmers will know how to design this software module 310.

Above are described preferred, but optional processing steps of generating an approximating function (see X*(t) in FIG. 6 and the related discussion), sampling the generated function, and then low-pass filtering the sampled values. Software modules 312, 313, 314 are included to perform these functions, and can be programmed using know techniques. Of course, any or all of these modules may be combined into a single body of code; they are shown separately for the sake of clarity. Also, if the measured or calculated values used as the basis for the approximating function are not std(P(k)), then the module 310 will be replaced, reprogrammed or omitted as needed to provide the appropriate values.

The std(P(k)) values, which will typically be stored in the memory 301, are then passed to a software module 320 that includes computer-executable code for detecting the maximum, minimum std(P(t)) values std(P)$_{max}$ and std(P)$_{min}$ and for computing the mean std(P(t)) value mean(std(P(k)) for each given computation/measurement interval, which may be triggered by a respiratory device 325 such as a ventilator or detected by a software module as described above. Again, even moderately skilled programmers will know how to design the software module 320 given the description above. Also as noted above, if the computation interval is chosen to extend over more than one respiratory cycle, then it will not be necessary to calculate the maximum and minimum std(P(t)) values std(P)$_{max}$ and std(P)$_{min}$ such that the module 320 can be omitted or at least not called.

The values std(P)$_{max}$, std(P)$_{min}$ and mean(std(P(k)) are then passed to an SVV calculation module 330, which computes an estimate of SVV for the chosen interval according to Equation 8 or 9. If a multi-cycle interval is set, then the SVV calculation module 320 may operate directly on the std(P(k)) values provided by module 310 to calculate an estimate of SVV according to Equation 10.

As shown in FIG. 7, any or all of the software modules 306, 310, 312-314, 320, and 330 may be implemented simply as routines within a single estimation software component 370, which may of course be combined with other software components of the processing system 300 as desired.

The invention further relates to a computer program loadable in a computer unit or the processing system 300 in order to execute the method of the invention. Moreover, the various software modules 310, 312-314, 315 (if implemented in software), 320, 330, or, in general, 370, used to perform the various calculations and perform related method steps according to the invention may also be stored as computer-executable instructions on a computer-readable medium in order to allow the invention to be loaded into and executed by different processing systems.

Once an SVV (or other cardiac or hemodynamic) estimate has been computed, it is passed to any desired output device 500, such as a user-viewable monitor, and displayed, stored or transmitted in any chosen format. An input device 400 is preferably also included to allow the user to input, for example, administrative and patient-specific information, to adjust the display, to choose the computation interval, etc. Note that if the user is to be allowed to change the computation interval, then the corresponding information must be made available to the estimation software component 370 so that it can direct the SVV estimation module to select the required input values when computing SVV according to either Equations 8 or 9, or Equation 10.

Test Results

Two different but related methods for computing SVV from std(P(k)) values are described above—one in which SVV is calculated for over single respiratory cycles and another that may be used to compute a single SVV value for a computation interval spanning more than one respiratory cycle. The inventors tested both these embodiments of the invention on animal femoral and radial blood pressure data. The data were collected from several pig experiments, which were performed in a laboratory. During the experiments, several changes in the left ventricular volume were induced (such as volume infusions or volume extractions). Variations of the peripheral resistance (vasodilation or vasoconstriction) were induced as well. Both embodiments of the invention were found not only to provide similar SVV estimates, but also these estimates were found to be superior to those obtained using prior art methods for the sake of comparison.

Additional Outputs

As mentioned above, the invention may be used to estimate not only SVV, but also any cardiac parameter that can be derived from SVV. The inventors have discovered in tests, for example, that during mechanical ventilation with a constant ventilation rate and a constant tidal volume the right ventricular end diastolic volume (EDV) is an inversely proportional to SVV. Thus:

$$EDV = c/SVV \qquad \text{(Equation 11)}$$

where c is a calibration factor, which may be constant. The SVV estimate provided by the invention could therefore be used as an indirect method to estimate EDV, ejection fraction or other values that are known to be proportional to the degree of vascular filling.

The calibration factor c in Equation 11 will depend on several parameters such as ventricular contractility and ventricular compliance. In general, c will depend on the hemodynamic state of the patient. Recalibration must therefore be performed each time the hemodynamic status of the patient changes or during periods of hemodynamic instability.

We claim:

1. A method for determining a cardiac parameter equal to or derivable from cardiac stroke volume variation (SVV) comprising:
   inputting a waveform data set corresponding to arterial blood pressure over a computation interval that covers at least two cardiac cycles;
   calculating a standard deviation value for the waveform data set over each cardiac cycle; and
   calculating an estimate of the SVV as a function of the standard deviation values.

2. A method as in claim 1, further comprising:
   over the computation interval, determining maximum and minimum standard deviation values; and
   calculating the estimate of the SVV as a function of the maximum and minimum standard deviation values.

3. A method as in claim 2, further comprising:
   over the computation interval, computing mean standard deviation value; and
   calculating the estimate of the SVV to be proportional to the difference between the maximum and minimum standard deviation values relative to the mean standard deviation value.

4. A method as in claim 1, further comprising:
   detecting the boundaries of respiratory cycles; and
   setting the computation interval to be at least one respiratory cycle.

5. A method as in claim 4, further comprising:
   computing the standard deviation of the standard deviation values over the computation interval;
   computing the mean of the standard deviation values over the computation interval; and
   calculating the estimate of the SVV proportional to the ratio between the standard deviation of the standard deviation values and the mean of the standard deviation.

6. A method as in claim 1, further comprising:
   measuring arterial pressure using a catheter-mounted pressure transducer; and
   converting the measured arterial pressure into the waveform data set.

7. A method as in claim 1, further comprising:
   measuring arterial pressure non-invasively; and
   converting the measured arterial pressure into the waveform data set.

8. A method as in claim 1, further comprising calculating an estimate of right ventricular end diastolic volume as being inversely proportional to the calculated estimate of the cardiac stroke volume variation.

9. A method as in claim 1, further comprising:
   computing an approximating function that best matches the calculated standard deviation values according to a predetermined metric over at least one of the computation intervals;
   creating a set of sampled, approximating values by sampling the approximating function at an interval-specific sampling rate;
   low-pass filtering the sampled, approximating values; and
   calculating the estimate of the SVV as a function of the low-pass filtered, sampled approximating values.

10. A system for determining a cardiac parameter equal to or derivable from cardiac stroke volume variation (SVV) comprising:
    an arrangement for determining and inputting a waveform data set corresponding to arterial blood pressure over a computation interval that covers at least two cardiac cycles;
    a processing system including computer-executable code
    for calculating a standard deviation value for the waveform data set over each cardiac cycle; and
    for calculating an estimate of the SVV as a function of the standard deviation values.

11. A system as in claim 10, in which the processing system further includes additional computer-executable code:
    for determining maximum and minimum standard deviation values over the computation interval; and
    for calculating the estimate of th SVV as a function of the maximum and minimum standard deviation values.

12. A system as in claim 11, in which the processing system further includes additional computer-executable code
    for computing a mean standard deviation value over the computation interval; and
    for calculating th estimate of the SVV to be proportional to the difference between the maximum and minimum standard deviation values relative to the mean standard deviation value.

13. A system as in claim 10, further comprising a mechanism for detecting the boundaries of respiratory cycles, in which the computation interval is at least one respiratory cycle.

14. A system as in claim 13, in which the processing system further includes additional computer-executable code
    for computing the standard deviation of the standard deviation values over the computation interval;
    for computing the mean of the standard deviation values over the computation interval; and
    for calculating the estimate of the SVV proportional to the ratio between the standard deviation of the standard deviation values and the mean of the standard deviation.

15. A system as in claim 10, further comprising:
    a catheter-mounted pressure transducer measuring arterial blood pressure; and
    conversion circuitry converting the measured arterial pressure into the waveform data set.

16. A system as in claim 10, further comprising:
    a non-invasive arterial pressure measurement device; and
    conversion circuitry converting the measured arterial pressure into the waveform data set.

17. A system as in claim 10, in which the processing system further includes additional computer-executable code for calculating an estimate of right ventricular end diastolic volume as being inversely proportional to the calculated estimate of the cardiac stroke volume variation.

18. A system as in claim 10, in which the processing system further includes a low-pass filter and additional computer-executable code
    for computing an approximating function that best matches the calculated standard deviation values according to a predetermined metric over at least one of the computation intervals;
    for creating a set of sampled, approximating values by sampling the approximating function at an interval-specific sampling rate; and
    for calculating the estimate of the SVV as a function of the low-pass filtered, sampled approximating values filtered by the low-pass filter.

* * * * *